United States Patent
Cathier et al.

(10) Patent No.: US 12,303,251 B2
(45) Date of Patent: May 20, 2025

(54) CAVITY DETERMINATION APPARATUS

(71) Applicant: KONINKLIJKE PHILIPS N.V., Eindhoven (NL)

(72) Inventors: Pascal Yves Francois Cathier, Asnières-sur-Seine (FR); Olivier Pierre Nempont, Suresnes (FR); Raoul Florent, Ville D'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 459 days.

(21) Appl. No.: 16/242,313

(22) Filed: Jan. 8, 2019

(65) Prior Publication Data

US 2019/0133492 A1    May 9, 2019

Related U.S. Application Data

(63) Continuation of application No. 14/405,559, filed as application No. PCT/IB2013/055057 on Jun. 20, 2013, now Pat. No. 10,182,745.

(30) Foreign Application Priority Data

Jun. 22, 2012  (EP) .................................... 12305719

(51) Int. Cl.
   *A61B 5/107*      (2006.01)
   *A61B 5/00*       (2006.01)
   (Continued)

(52) U.S. Cl.
   CPC ............ *A61B 5/1076* (2013.01); *A61B 5/065* (2013.01); *A61B 5/1077* (2013.01); *A61B 5/287* (2021.01);
   (Continued)

(58) Field of Classification Search
   CPC .............................. A61B 5/1076; A61B 5/065
   See application file for complete search history.

(56) References Cited

U.S. PATENT DOCUMENTS

| | | |
|---|---|---|
| 5,718,241 A | 2/1998 | Ben-Haim et al. |
| 5,738,096 A | 4/1998 | Ben-Haim |
| (Continued) | | |

FOREIGN PATENT DOCUMENTS

| | | |
|---|---|---|
| JP | 2011217835 A | 11/2010 |
| WO | 1996005768 A1 | 2/1996 |
| WO | 2008052274 A | 5/2008 |

*Primary Examiner* — Alex M Valvis
*Assistant Examiner* — Yasmeen S Warsi

(57) ABSTRACT

The invention relates to a cavity determination apparatus for determining a cavity within an object, in particular, for determining the location and dimensions of a heart chamber within a person without use of electrode contact information. A bendable segment of an introduction element is arranged within the cavity in different arrangements, wherein curves defined by the bendable segment in the different arrangements are determined by a curve determination unit. A cavity reconstruction unit reconstructs the cavity based on the determined curves. Thus, not only single locations within the cavity are acquired and used for reconstructing the cavity, but larger curves. A considerable amount of spatial information can therefore be acquired and used very rapidly. This allows reconstructing the cavity with improved quality in a relatively short time.

20 Claims, 3 Drawing Sheets

(51) Int. Cl.
  *A61B 5/06* (2006.01)
  *A61B 5/287* (2021.01)
(52) U.S. Cl.
  CPC .......... *A61B 5/6852* (2013.01); *A61B 5/6886* (2013.01); *A61B 5/7207* (2013.01); *A61B 5/742* (2013.01); *A61B 2562/0266* (2013.01); *A61B 2562/164* (2013.01); *A61B 2576/023* (2013.01)

(56) References Cited

U.S. PATENT DOCUMENTS

| | | | |
|---|---|---|---|
| 6,063,022 A | 6/2000 | Ben-Haim | |
| 6,272,371 B1 | 8/2001 | Ben-Haim | |
| 6,301,496 B1 | 10/2001 | Reisfeld | |
| 6,892,091 B1 * | 5/2005 | Ben-Haim | A61B 5/287 |
| | | | 600/509 |
| 7,813,599 B2 | 10/2010 | Moore | |
| 8,075,498 B2 | 12/2011 | Leo et al. | |
| 8,359,092 B2 | 1/2013 | Hayam et al. | |
| 2003/0099384 A1 | 5/2003 | Zeng et al. | |
| 2003/0231789 A1 | 12/2003 | Willis et al. | |
| 2004/0097805 A1 * | 5/2004 | Verard | A61B 1/00071 |
| | | | 600/428 |
| 2006/0064006 A1 * | 3/2006 | Strommer | A61B 8/12 |
| | | | 600/415 |
| 2009/0076476 A1 | 3/2009 | Barbagli et al. | |
| 2010/0268059 A1 | 10/2010 | Ryu et al. | |
| 2011/0007937 A1 | 1/2011 | Yan et al. | |
| 2011/0022045 A1 | 1/2011 | Cao et al. | |
| 2011/0130648 A1 | 6/2011 | Beeckler et al. | |
| 2011/0137153 A1 * | 6/2011 | Govari | A61B 5/062 |
| | | | 600/424 |
| 2012/0004540 A1 | 1/2012 | Lin et al. | |
| 2014/0023250 A1 | 1/2014 | Cathier et al. | |
| 2015/0133822 A1 | 5/2015 | Cathier | |

* cited by examiner

CAVITY DETERMINATION APPARATUS

CROSS-REFERENCE TO PRIOR APPLICATIONS

This application is a continuation of application Ser. No. 14/405,559 filed Dec. 14, 2014. Application Ser. No. 14/405,559 is the U.S. National Phase application under 35 U.S.C. § 371 of International Application Serial No. PCT/IB2013/055057, filed on Jun. 20, 2013, which claims the benefit of EP Application Serial No. 12305719.2, filed on Jun. 22, 2012. This application is hereby incorporated by reference herein.

FIELD OF THE INVENTION

The invention relates to a cavity determination apparatus, a cavity determination method and a cavity determination computer program for determining a cavity within an object.

BACKGROUND OF THE INVENTION

US 2010/0268059 A1 discloses an ablation system for ablating cardiac tissue. The system comprises an ablation catheter with an electromagnetic localization sensor located close to the tip of the ablation catheter. The tip of the catheter is moved to different locations on the inner wall of the heart, wherein at each location the position of the tip is determined by using the localization sensor. The resulting set of determined positions is used for reconstructing an inner cavity of the heart.

Since in an acceptable time only few different positions of the tip of the ablation catheter within the cavity can be determined, the reconstructed cavity, which is determined based on only these few locations of the tip of the ablation catheter, has a poor quality only.

SUMMARY OF THE INVENTION

It is an object of the present invention to provide a cavity determination apparatus, a cavity determination method and a cavity determination computer program for determining a cavity within an object, which allows determining the cavity within the object with improved quality in a relatively short time.

In a first aspect of the present invention a cavity determination apparatus for determining a cavity within an object is presented, wherein the apparatus comprises:
  an introduction element for being introduced into the cavity, wherein the introduction element comprises a bendable segment for being arranged within the cavity in different arrangements,
  a curve determination unit for determining curves defined by the bendable segment within the cavity in the different arrangements,
  a cavity reconstruction unit for reconstructing the cavity based on the determined curves.

Since not only single locations within the cavity are acquired, but curves defined by the bendable segment within the cavity in the different arrangements, a lot of spatial information can be acquired very fast. This allows reconstructing the cavity with improved quality in a relatively short time.

The determined curve defined by the bendable segment within the cavity in the respective arrangement can be regarded as a one-dimensional line describing the shape, orientation and location of the bendable segment within the cavity in the respective arrangement. The determined curve can therefore be regarded as describing the spatial run of the bendable segment within the cavity in the different arrangements.

The introduction element is preferentially a catheter, in particular, an ablation catheter for ablating an inner wall of the cavity. Preferentially, the cavity is a cavity of a heart of a living being and the ablation catheter is adapted to ablate cardiac tissue.

In an embodiment the cavity reconstruction unit is adapted to reconstruct the cavity such that the determined curves defined by the bendable segment in the different arrangements are within the reconstructed cavity. Moreover, at least in some of the different arrangements the bendable segment can be in contact with the inner wall of the cavity such that the curves define contact curves, wherein the cavity reconstruction unit can be adapted to reconstruct the cavity depending on the contact curves. In particular, the cavity reconstruction unit can be adapted to reconstruct the cavity such that walls of the reconstructed cavity correspond to the contact curves. For instance, the cavity reconstruction unit can be adapted to reconstruct the cavity such that the walls of the reconstructed cavity run through the contact curves and/or enclose the contact curves. This allows reconstructing the cavity reliably based on the contact curves.

In a preferred embodiment the introduction element comprises at least two electrodes between which the bendable segment is located, wherein the apparatus comprises a contact determination unit, which is electrically connected to the at least two electrodes, for determining contact information indicating whether the bendable segment is in contact with the inner wall of the cavity based on electrical signals received from the electrodes, wherein the cavity reconstruction unit is adapted to determine whether determined curves are contact curves depending on the contact information. The contact determination unit is preferentially adapted to determine that the bendable segment is in contact with the inner wall of the cavity, if the electrical signals received from the electrodes indicate that the electrodes are in contact with the inner wall. This allows the apparatus to reliably determine whether the bendable segment is in contact with the inner wall of the cavity or not in the respective arrangement such that contact curves can reliably be determined.

In some of the different arrangements the bendable segment may not be in contact with the inner wall of the cavity such that the curves defined by the bendable segment are non contact curves, wherein the cavity reconstruction unit can be adapted to reconstruct the cavity depending on the contact curves and depending on the non contact curves. The cavity reconstruction unit can be adapted to reconstruct the cavity such that the non contact curves are within the reconstructed cavity. The consideration also of the non contact curves, while reconstructing the cavity, can further improve the quality of the reconstruction.

The cavity reconstruction unit can also be adapted to determine whether determined curves are non contact curves depending on the contact information provided by the contact determination unit. The at least two electrodes and the contact determination unit can therefore also be used to reliably determine non contact curves, which can be used together with contact curves for reconstructing the cavity.

In an embodiment the cavity reconstruction unit is adapted to provide an adaptable cavity model and to adapt the cavity model to the determined curves defined by the bendable segment in the different arrangements for reconstructing the cavity. The cavity model may be a generic model or an object-specific model, in particular, a patient-specific model. It is preferentially an anatomical model. The cavity model is, for instance, a model of a cavity of a heart of a living being, which is adapted to, for instance, the contact curves. The use of the cavity model can further improve the quality of reconstructing the cavity.

The cavity model can be adapted such that the determined curves defined by the bendable segment in the different arrangements are within the cavity model, i.e. such that the determined curves defined by the bendable segment in the different arrangements are enclosed by the adapted cavity model. If at least some of the determined curves defined by the bendable segment within the cavity in the different arrangements form contact curves, the cavity model can be adapted to these contact curves such that the contact curves correspond to the outer surface of the cavity model. If at least some of the determined curves defined by the bendable segment within the cavity in the different arrangements are not contact curves, the cavity model can be adapted to wrap these determined curves. The cavity model can be regarded as a regularization, which can be used to reconstruct the cavity based on a determined set of curves defined by the bendable segment within the cavity in the different arrangements. Alternatively or in addition, also another regularization can be used. For instance, the cavity reconstruction unit can be adapted to perform a morphological opening or closing of the determined curves defined by the bendable segment within the cavity in the different arrangements for reconstructing the cavity.

In particular, if the determined curves defined by the bendable segment are non contact curves, these non contact curves lie within the cavity and the surface of the cavity has to be estimated from these curves. The regularization preferentially defines which points are likely to be within the cavity and which points are likely to be outside the cavity based on the non contact curves, in order to determine the surface of the cavity. This regularization can be model-based, wherein the regularization is performed such that the cavity model, which is preferentially an anatomical model, wraps the set of non contact curves. If prior anatomical information, i.e. an anatomical cavity model, is not present, homogenous mathematical regularization can be used by the cavity reconstruction unit. For instance, a morphological opening of the curve set can be used for estimating which points lie necessarily within the cavity.

In another embodiment the cavity reconstruction unit is adapted to interpolate the determined curves defined by the bendable segment in the different arrangements for reconstructing the cavity. For instance, it can be interpolated between contact curves for determining the cavity. The interpolation procedure can use, for example, triangulation, Fourier-based interpolation or another interpolation technique. Thus, the cavity reconstruction unit can be adapted to reconstruct the cavity, without using prior information like an object-specific model.

The interpolation of the determined curves defined by the bendable segment in the different arrangements for reconstructing the cavity can be combined with a regularization. For instance, the regularization could be performed by switching from an interpolation constrain to an energy-based fitting of a cavity model. This allows improving the quality of the reconstructed cavity, if the determined curves defined by the bendable segment in the different arrangements are noisy.

It is preferred that the object is a living being, wherein the cavity is influenced by at least one of cardiac motion and respiratory motion, wherein the apparatus comprises a motion signal providing unit for providing a motion signal being indicative of at least one of a) different cardiac phases and b) different respiratory phases, wherein the cavity reconstruction unit is adapted to reconstruct the cavity based on the determined curves defined by the bendable segment and based on the provided motion signal. By considering the motion signal, i.e. the cardiac signal and/or the respiratory signal, while reconstructing the cavity, the reconstruction may comprise less motion artifacts. Preferentially, based on the motion signal each determined curve defined by the bendable segment can be assigned to a certain motion phase, i.e. to a certain cardiac phase and/or to a certain respiratory phase, wherein this assigned phase information can be used to reconstruct the cavity with reduced motion artifacts. For instance, the cavity reconstruction unit can be adapted to use curves only, which correspond to the same motion phase, in order to reconstruct a cavity, which corresponds to this certain motion phase.

The curve determination unit can be adapted to determine the position of at least a part of the introduction element being in contact with a part of the living being, which moves in accordance with at least one of the cardiac cycle and the respiratory cycle, over time, thereby determining a movement of the part of the introduction element, wherein the motion signal providing unit can be adapted to determine the motion signal depending on the determined movement. For instance, the curve determination unit can be adapted to determine the position of an electrode of the introduction element, while the electrode is in contact with an inner wall of a heart, over time, thereby determining the movement of the electrode. Since the electrode is in contact with the inner wall of the heart, the movement of the electrode is likely to be periodic in accordance with the cardiac cycle such that the cardiac signal can be determined depending on the movement of the electrode. Also the position of another part of the introduction element may be determined over time, while this part is in contact with a part of, for instance, a person moving in accordance with the cardiac cycle or the respiratory cycle, in order to determine the motion signal depending on the movement of this part of the introduction element. Respiratory motion may be estimated using the shape of a catheter, while a part of the catheter abuts against a part of an anatomy of a person that experiences pure respiratory motion or from which respiratory motion can be estimated. Also a further shape sensing catheter can be used for determining respiratory motion in the same way. Moreover, other means can be used for providing a motion signal. For instance, an electrocardiograph can be used for providing a cardiac signal, a respiratory belt can be used for providing a respiratory signal, a respiratory signal can be determined based on an analysis of a video showing the moving thorax of a person, et cetera.

The introduction element and the curve determination unit are preferentially adapted to determine the curves defined by the bendable segment within the cavity by optical shape sensing. This allows the apparatus to reliably determine the different curves defined by the bendable segment within the cavity, without necessarily requiring further localization units like an electromagnetic localization unit or an x-ray localization unit.

In a further aspect of the present invention a cavity determination method for determining a cavity within an object is presented, wherein the method comprises:

determining curves defined by a bendable segment of an introduction element introduced into the cavity in different arrangements within the cavity by a curve determination unit, and reconstructing the cavity from the determined curves by a cavity reconstruction unit.

In another aspect of the present invention a cavity determination computer program for determining a cavity within an object is presented, wherein the computer program comprises program code means for causing a cavity determination apparatus to carry out the steps of a cavity determination method, described herein, when the computer program is run on a computer controlling the cavity determination apparatus.

It shall be understood that the cavity determination apparatus, the cavity determination method and the cavity determination computer program of the independent claims have similar and/or identical embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
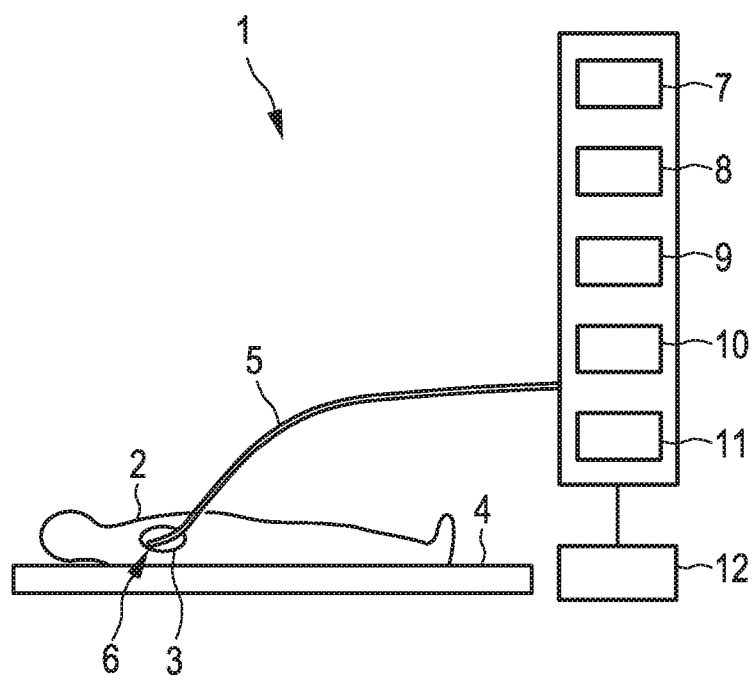
FIG. 1 shows schematically and exemplarily an embodiment of a cavity determination apparatus for determining a cavity within an object.

FIG. 1 shows schematically and exemplarily an embodiment of a cavity determination apparatus for determining a cavity within an object. The apparatus 1 comprises an introduction element 5 for being introduced into the cavity 3, wherein the introduction element 5 comprises a bendable segment for being arranged within the cavity 3 in different arrangements. In this embodiment the object is a person 2 lying on a table 4 and the cavity 3 is a chamber of the heart of the person 2. Moreover, in this embodiment the introduction element 5 is an ablation catheter, wherein the tip 6 of the ablation catheter 5 has been introduced into the cavity 3. The bendable segment of the ablation catheter 5 is located at the tip 6 of the ablation catheter 5 and can be positioned, i.e. bent, oriented and/or located, within the cavity 3 such that it conforms with an inner wall of the cavity 3, in order to bring the bendable segment into contact with the inner wall.

The cavity determination apparatus 1 further comprises a curve determination unit 7 for determining curves defined by the bendable segment within the cavity 3 in the different arrangements and a cavity reconstruction unit 8 for reconstructing the cavity based on the determined curves.

Preferentially, the bendable segment of the ablation catheter 5 is arranged in different arrangements within the cavity 3 such that in at least some of these arrangements the bendable segment conforms with the inner wall of the cavity 3 and is thus in contact with the inner wall of the cavity 3. In this case, the determined curves define contact curves, wherein the cavity reconstruction unit 8 is adapted to reconstruct the cavity depending on these contact curves, i.e. depending on the respective shape, orientation and location of the respective contact curve. In particular, the cavity reconstruction unit 8 can be adapted to reconstruct the cavity such that walls of the reconstructed cavity are defined by the contact curves.

The cavity reconstruction unit 8 can be adapted to provide an adaptable cavity model and to adapt the cavity model to the contact curves for determining the cavity. Thus, the cavity model, which can also be regarded as being an existing template of the cavity, which may be generic or person specific, can be fitted to the contact curves. The cavity model can be arranged and/or deformed such that the walls of the cavity model are defined by the contact curves.

If at least some of the determined curves defined by the bendable segment within the cavity in the different arrangements are not contact curves or if, in an embodiment, it is not known whether the determined curves are contact curves or non contact curves, the cavity model can be adapted to wrap the determined curves defined by the bendable segment within the cavity in the different arrangements. The cavity model can be regarded as a kind of regularization, which can be used to reconstruct the cavity based on a determined set of curves defined by the bendable segment within the cavity in the different arrangements. Alternatively or in addition, also another regularization can be used, in particular, if all determined curves are non contact curves or if it is not known whether the determined curves are contact curves or non contact curves. For instance, the cavity reconstruction unit can be adapted to perform a morphological opening or closing of the determined curves defined by the bendable segment within the cavity in the different arrangements for reconstructing the cavity.

The cavity reconstruction unit 8 can also be adapted to reconstruct the cavity by interpolating the determined contact curves, wherein the interpolation can include, for example, a triangulation, a Fourier-based interpolation or another interpolation technique. Thus, the cavity may be reconstructed "from scratch", i.e. using the sample shapes, i.e. the sampled contact curves, without any prior data. This kind of reconstruction relies on the assumption that what constitutes the volume of the cavity, i.e. the inside of the cavity, can be inferred from the contact curves.

The interpolation of the determined curves defined by the bendable segment in the different arrangements for reconstructing the cavity can be combined with a regularization, in order to improve the quality of the reconstructed cavity, particularly if the determined curves defined by the bendable segment in the different arrangements are noisy.

Figure 2:
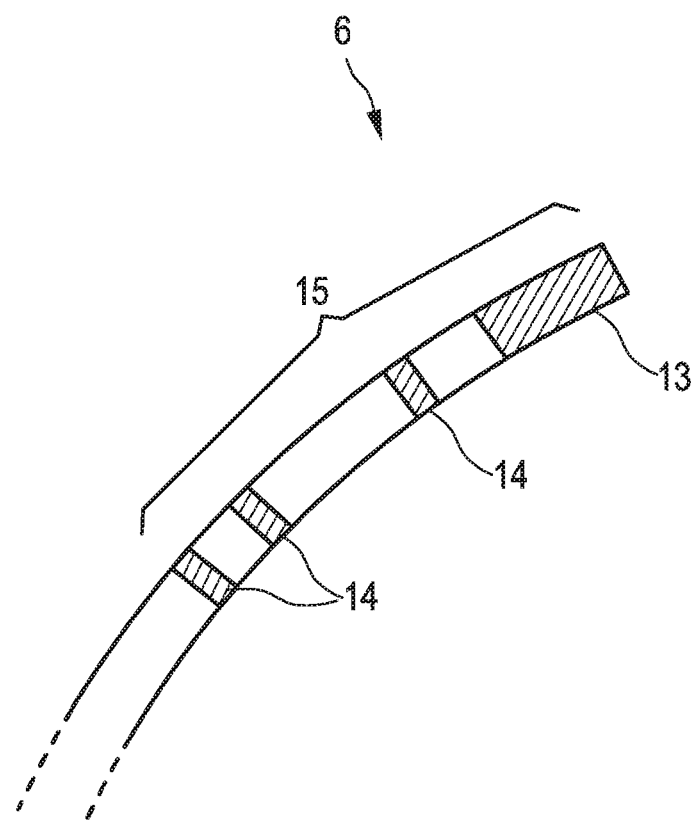
FIG. 2 shows schematically and exemplarily a tip of a catheter of the cavity determination apparatus.

FIG. 2 shows schematically and exemplarily the tip 6 of the introduction element 5 in more detail. The tip 6 of the introduction element 5 comprises several ring electrodes 14 and a cap electrode 13. These electrodes 13, 14 are arranged along the bendable segment 15, wherein the bendable segment can also be larger than indicated in FIG. 2. The apparatus 1 further comprises a contact determination unit 9, which is electrically connected to the electrodes 13, 14, for determining contact information indicating whether the bendable segment 15 is in contact with a wall of the cavity based on electrical signals received from the electrodes 13, 14, wherein the cavity reconstruction unit 8 is adapted to determine whether the determined curves are contact curves depending on the contact information. In particular, the contact determination unit 9 is adapted to determine that the bendable segment is in contact with the inner wall of the cavity, i.e. conforms to the inner wall of the cavity, if the electrical signals received from all electrodes 13, 14 indicate that the electrodes 13, 14 are in contact with the inner wall.

If the electrodes 13, 14 are not in contact with the cardiac tissue of the inner wall of the cavity, they substantially do not receive any electrical signal, i.e. the output of the electrodes is mostly flat. If the electrodes are in contact with the cardiac tissue, they detect a periodic electrical signal. Based on these differences in electrical detection the contact determination unit 9 can determine whether all electrodes 13, 14 and, thus, the bendable segment 15 are in contact with the inner wall of the cavity, i.e. whether the bendable segment 15 conforms to the inner wall of the cavity.

In some of the different arrangements the bendable segment may not conform to the inner wall of the cavity 3 and may therefore be not in contact with the inner wall such that the determined curves are non contact curves, wherein the cavity reconstruction unit 8 can be adapted to reconstruct the cavity also depending on the non contact curves. In particular, the cavity reconstruction unit 8 can be adapted to reconstruct the cavity such that positions of the non contact curves are within the reconstructed cavity. For determining the non contact curves, the electrodes 13, 14 can be used, which are also used for determining the contact curves. In particular, the cavity reconstruction unit can be adapted to determine whether determined curves are non contact curves depending on the contact information provided by the electrodes 13, 14, wherein it is assumed that the bendable segment 15 is not in contact with the inner wall of the cavity in the respective arrangement, if not all electrodes 13, 14 arranged along the bendable segment are in contact with the inner wall of the cavity 3. If two consecutive electrodes are in contact with the inner wall of the cavity, it is assumed that the segment of the catheter between these two consecutive electrodes is in contact with the inner wall, i.e. that this intermediate segment forms a contact curve.

If non contact curves are used for reconstructing the cavity, the electrical signals provided by the electrodes may be ignored. For instance, a bendable segment of the introduction element before the first proximal electrode may be used for defining non contact curves. Generally, all parts of the introduction element, which are not located between contact electrodes, can be regarded as defining non contact curves.

The apparatus 1 is preferably adapted to allow a user like a physician to arrange the bendable segment at the tip 6 of the catheter 5 in different arrangements within the cavity 3, wherein, after the user has arranged the bendable segment in a desired arrangement, the curve determination unit 7 can determine the curve defined by the bendable segment within the cavity 3 in this certain arrangement. In this way, different curves defined by the bendable segment within the cavity in the different arrangements can be determined, wherein, after these different curves have been determined in the different arrangements, the cavity reconstruction unit 8 can be used to reconstruct the cavity based on these determined curves.

The cavity 3 is influenced by cardiac motion. The apparatus therefore further comprises a motion signal providing unit 10 for providing a motion signal being indicative of the different cardiac phases of the heart of the person 3, wherein the cavity reconstruction unit 8 is adapted to reconstruct the cavity based on the determined curves defined by the bendable segment in the different arrangements, in particular, depending on the determined contact curves and optionally also on the determined non contact curves, and based on the provided motion signal. In this embodiment, the curve determination unit 7 is adapted to determine the position of a part of the catheter 5 being in contact with a part of the person 2, which moves in accordance with the cardiac cycle, over time, thereby determining a movement of this part of the catheter 5, wherein the motion signal providing unit 10 is adapted to determine the motion signal depending on the determined movement. For instance, the curve determination unit 7 can be adapted to determine the position of one of the contact electrodes, which can be used for determining whether the bendable segment is in contact with the inner wall of the cavity or not, while the contact electrode is in contact with the inner wall of the cavity, wherein it is assumed that the inner wall of the cavity being, in this embodiment, the heart of the person moves in accordance with the cardiac cycle. The cyclic motion of the part of the catheter 5, which is in contact with the inner wall of the cavity 3 and which is preferentially a contact electrode, can be subdivided into several parts for defining and determining the cardiac phases of the cardiac cycle. The determined curves defined by the bendable segment in the different arrangements can be assigned to these cardiac phases, wherein the cavity reconstruction unit 8 can be adapted to reconstruct the cavity based on determined curves, which are assigned to a single cardiac phase only. This allows reconstructing the cavity with reduced motion artifacts. In particular, for each cardiac phase a respective cavity can be reconstructed, wherein the different reconstructed cavities, which correspond to different cardiac phases, can be shown temporarily consecutively on a display unit 12 for providing a four-dimensional image of the cavity.

The curves defined by the bendable segment within the cavity 3 in the different arrangements can be determined in a breathhold condition such that respiratory motion does not adversely affect the reconstruction of the cavity. However, the motion signal providing unit can also be adapted to additionally provide a further motion signal being a respiratory signal, which is indicative of different respiratory phases, wherein the cavity reconstruction unit can be adapted to reconstruct the cavity based on the first motion signal being a cardiac signal, which is indicative of the cardiac phases, and the respiratory signal. The respiratory signal may be determined by the motion signal providing unit based on a determined movement of a part of the catheter 5, which is in contact with an anatomical part of the person 2, which moves only in accordance with the respiratory cycle. This movement can be determined by the curve determination unit 7, which may determine the position of this part over time. The cavity reconstruction unit 8 can then be adapted to reconstruct the cavity for a certain cardiac phase and for a certain respiratory phase based on the determined curves, which are assigned to this certain cardiac phase and this certain respiratory phase. Also in this case the cavity can be reconstructed for different cardiac phases and for different respiratory phases, wherein the resulting reconstructed cavities can be shown temporarily consecutively on the display unit 12 for providing a four-dimensional reconstructed cavity.

The catheter 5 and the curve determination unit 7 are preferentially adapted to determine the curves defined by the bendable segment within the cavity 3 and also the position of further parts of the catheter 5 by optical shape sensing.

The apparatus 1 further comprises an RF power source 11 for providing power to the cap electrode 13 of the catheter 5, which is located at the tip 6 of the catheter 5. This allows a physician to ablate cardiac tissue at a desired location within the cavity 3 depending on the reconstruction of the cavity shown on the display unit 12.

The cap electrode 13 is therefore not only used for determining whether the bendable segment 15 is in contact with the inner wall of the cavity or not, but also for performing an ablation procedure. In other embodiments contact electrodes for determining, whether the bendable segment is in contact with the inner wall of the cavity and one or several ablation electrodes can be different electrodes, i.e. the ablation electrodes may not be used for providing the contact information.

Figure 3:
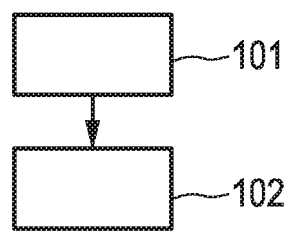
FIG. 3 shows a flowchart exemplarily illustrating an embodiment of a cavity determination method for determining a cavity within an object.

In the following an embodiment of a cavity determination method for determining a cavity within an object will exemplarily be described with reference to a flowchart shown in FIG. 3.

In step 101 the bendable segment of the introduction element is arranged in different arrangements within the cavity, wherein in each arrangement the curve defined by the bendable segment is determined by a curve determination unit. Thus, the shape, orientation and location of the bendable segment is determined in each arrangement. Moreover, preferentially electrodes enclosing the bendable segment, in particular, being arranged along the bendable segment, are used together with a contact determination unit for determining whether the bendable segment conforms to the inner wall of the cavity, i.e. is in contact with the inner wall of the cavity, in the respective arrangement. This allows determining contact curves defined by the bendable segment in arrangements in which the bendable segment is in contact with the inner wall of the cavity, and non contact curves defined by the bendable segment in arrangements in which the bendable segment is not in contact with the inner wall of the cavity.

In step 102 the cavity is reconstructed from the determined curves by a cavity reconstruction unit. In particular, an adaptable model may be adapted to the contact curves or the contact curves may be interpolated, in order to reconstruct the cavity.

The apparatus is preferentially adapted to perform a minimally invasive, transcatheter procedure. During those procedures the physician, for instance, a surgeon or a cardiologist, cannot observe tools and anatomy with the naked eye. Real-time imaging modalities such as x-ray modalities or ultrasound modalities provide partial solutions to this problem, but they have their own limitations. In some interventional procedures like atrial fibrillation ablation such imaging modalities may be skipped in the prior art, wherein instead a positioning device like a magnetic-based positioning device attached to an ablation catheter may be used to reconstruct the cavity of, for instance, the left atrium. However, using such a positioning device has at least two major problems. The use of a single position or of even few positions for reconstructing the cavity yields scarce data, the acquisition times are rather long and the modeling quality it relatively low.

The apparatus described above with reference to FIGS. 1 and 2 is therefore preferentially adapted such that the positioning device can be replaced by a shape sensing device, which enables the reconstruction to be based on curves, rather than points, in a much faster fashion. In particular, shape sensing technology is preferentially used, in order to recover very quickly the shape of the cavity. Preferentially, the shape of the device, i.e. the shape of the bendable segment, is collected, while the device is moved inside the target cavity. As the device lies inside the cavity, the cavity surface can be recovered as the "outer surface" of the collected shapes. In particular, a catheter may be moved rapidly and in a more or less random fashion to quickly get the bulk of the cavity, for instance, of the left atrium of a heart of a person. The outcome of the corresponding algorithm can then be used as a rough map to guide the catheter into areas where the acquisition should be refined, for instance, because of a particularly high interest in this area and/or because the area is more difficult to access due to larger curvatures which could have hampered a correct acquisition during the initial sweep. Higher curvatures may be present, for instance, in pulmonary veins.

For determining whether a point lying outside the acquired shapes, i.e. outside the set of determined curves defined by the bendable segment in the different arrangements within the cavity, belongs to the cavity or not, the apparatus can be adapted to use a regularity assumption. This regularity assumption can be expressed, for example, as a single mathematical opening or closure operation, or the regularity assumption could be a more complex and knowledge-based one based, for example, on a mesh template of the targeted cavity.

The apparatus is preferentially adapted to produce a consistent output, even if the cavity moves and/or deforms. Especially if the apparatus is used in cardiac applications, the apparatus can be adapted to handle with the deformations during the cardiac cycle and to consider respiratory motion as well. As the shape of the heart chambers deforms during the cardiac cycle, determined curves, which correspond to different cardiac phases, are preferentially not mixed. The apparatus can be adapted to reconstruct a three-dimensional model at a specific cardiac phase or at an indefinite cardiac phase, if the model is based on temporal averaging. The apparatus can also be adapted to reconstruct a four-dimensional model, i.e. a temporarily dependent spatially three-dimensional model of the cavity.

For identifying the cardiac phase and for assigning the identified cardiac phase to the respective determined curves the above described method can be used, which is based on the determination of the movement of a part of the introduction element, which moves in accordance with the cardiac cycle, because it is in contact with, for instance, an inner wall of a heart chamber. However, a cardiac signal can also be provided by other means. For example, a known electrocardiograph can be used for providing a cardiac signal. Moreover, it is also possible to determine the cardiac phase from the electrocardiography signal and from the determined motion of the part of the introduction element, which is in contact with, for instance, an inner wall of the heart chamber.

In order to mitigate a possible effect of respiratory motion on the quality of reconstructing the cavity, the acquisition, i.e. the determination of the curves defined by the bendable segment in the different orientations, can be performed at a given breathhold. Alternatively, the respiratory motion can be estimated using the shape of the introduction element, in particular, of the catheter, while a part of the introduction element lies against a part of the anatomy of the living being, from which respiratory motion can be estimated, in particular, which experiences pure respiratory motion.

Also a second shape sensing introduction element, in particular, a second shape sensing catheter, can be used in a similar fashion for determining respiratory motion. In this case, the first introduction element does not need to be guided through an area experiencing, for instance, pure respiratory motion, because the second shape sensing introduction element already provides the respiratory motion, which can be used for generating a respiratory signal. For example, in atrial fibrillation ablation procedures the coronary sinus catheter can be used as the second shape sensing introduction element in combination with heart motion cancellation techniques.

The respiratory motion can also be determined using other techniques like a respiratory belt, analyzing a video showing a part of the person, for instance, the thorax performing respiratory motion, et cetera.

Although in embodiments described above a possibly adverse effect on the reconstruction of the cavity due to respiratory motion is reduced by determining the curves defined by the bendable segment in the different arrangements in a breathhold condition or by reconstructing the cavity for a certain respiratory phase based on curves defined by the bendable segment in the different arrangements, which correspond to this certain respiratory phase, the adverse influence of the respiratory motion can also be reduced in another way. For instance, the determined curves defined by the bendable segment in the different arrangements can be corrected by a translational operation in accordance with the determined respiratory motion, wherein the cavity can be reconstructed based on the corrected curves.

The apparatus is preferentially adapted to model or fit an anatomical part, i.e. an anatomical cavity within a living being, based on a shape-sensing enabled catheter, preferentially without further requirements. It is further preferred that the apparatus uses large segments of the catheter for the determination of the cavity within the living being, i.e. the apparatus does preferentially not only use point positions as in the case of known electromagnetic tracking techniques, but the apparatus uses larger segments, which are larger than points on, for instance, a catheter.

The apparatus is preferentially adapted to use simultaneously shape sensing technology and multiple contact electrodes, wherein the contact of an electrode of the introduction element with the cavity is inferred based on the electrical signal measured by the respective electrode.

In an embodiment it is assumed that, when two electrodes are in contact, a part of the introduction element, i.e. the bendable segment, lying between them is also in contact with the cavity such that the shape of the introduction element between the two electrodes provided by shape sensing, which may define a respective contact curve, can be used for reconstructing the cavity. If the cavity curvature is very high in some areas, this assumption may be violated, thereby producing an under segmentation of the cavity. This under segmentation of the cavity can be corrected by inserting the introduction element inside the cavity. For instance, a catheter tip can be navigated to these areas and the position of the catheter tip can be determined, while the catheter tip is in these areas. These positions can be used together with the determined curves defined by the bendable segment in the different arrangements for reconstructing the cavity, wherein the cavity can be reconstructed such that the determined curves defined by the bendable segment in the different arrangements and also the determined positions of the catheter tip in the areas with the relatively high curvature are within the cavity. For instance, a cavity model can be adapted to these positions such that the cavity model encloses the different curves defined by the bendable segment and the positions of the catheter tip and such that the adapted cavity model conforms to these positions as good as possible.

Although in above described embodiments the introduction element comprises electrodes for determining whether the bendable segment is in contact with the inner wall of the cavity, in other embodiments the introduction element may not comprise electrodes for determining this contact information, in particular, the introduction element may not comprise any electrode or only electrodes for other purposes. In this case it is generally not known whether determined curves defined by the bendable segment are contact curves or non contact curves. However, also without this contact information the cavity reconstruction unit can reconstruct the cavity, for instance, by adaptating a cavity model, in particular, an anatomical cavity model, to the set of determined curves such that the determined curves are within the adapted cavity model and such that the adapted cavity model conforms as good as possible to the outer curves of the determined curves, or by performing, for instance, a morphological opening or closing of the set of curves.

The apparatus can also be adapted to record coordinates of curves that are not in contact with the cavity, i.e. to record non contact curves, in order to provide an indication of what constitutes the inside of the cavity. This could also be used at a final step to close holes in the reconstructed cavity due to non responsive tissues like scars or ablated areas.

The apparatus can be adapted to model or fit an anatomical part based on an introduction element with both shape sensing fibers and multiple electrodes, wherein shapes of a cavity can be reconstructed based on entire curves of the introduction element. The apparatus is preferentially adapted to be used in atrial fibrillation ablation procedures, in order to reduce the patient exposure to radiation, both before the operation and also after the operation.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of the cavity, i.e. the reconstruction of the cavity, the determination of the different curves defined by the bendable segment within the cavity in the different arrangements, the determination of the motion signal, et cetera performed by one or several units or devices can be performed by any other number of units or devices. The determinations and/or the control of the cavity determination apparatus in accordance with the cavity determination method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a cavity determination apparatus for determining a cavity within an object, in particular, for determining the location and dimensions of a heart chamber within a person. A bendable segment of an introduction element is arranged within the cavity in different arrangements, wherein curves defined by the bendable segment in the different arrangements are determined by a curve determination unit. A cavity reconstruction unit reconstructs the cavity based on the determined curves. Thus, not only single small locations within the cavity are acquired and used for reconstructing the cavity, but larger curves. A lot of spatial information can therefore be acquired and used very fast. This allows reconstructing the cavity with improved quality in a relatively short time.

The invention claimed is:

1. An apparatus for performing a minimally invasive medical procedure in a cavity of a subject, the apparatus comprising:
    a catheter for being introduced into the cavity, wherein the catheter is shape sensing enabled and comprises a bendable segment for being arranged within the cavity in different arrangements during the minimally invasive medical procedure; and
    a computer including a non-transitory storage medium for storing instructions that, when executed by the computer, cause the computer to:
        receive optical shape sensing information from the catheter;
        determine whether the bendable segment is in contact with an inner wall of the cavity in each arrangement of a plurality of different arrangements of the bendable segment introduced within the cavity;
        determine a plurality of curves defined by the bendable segment in the plurality of different arrangements of the bendable segment introduced within the cavity, respectively, using the optical shape sensing information from the catheter, wherein the plurality of curves comprise a plurality of contact curves corresponding to respective arrangements of the plurality of different arrangements of the bendable segment determined to be in contact with the inner wall of the cavity;
        reconstruct the cavity, in response to the plurality of contact curves, such that a reconstructed inner wall of the reconstructed cavity are defined by the plurality of contact curves; and
        display the reconstructed cavity to provide a map for guiding the catheter in the cavity to perform the minimally invasive medical procedure.

2. The apparatus of claim 1 further comprising a display device, operatively coupled to the computer, configured to display the reconstructed cavity.

3. The apparatus of claim 1, wherein the catheter comprises an ablation catheter, and wherein a distal tip of the ablation catheter is introduced into the cavity and the bendable segment is located at the distal tip.

4. The apparatus of claim 1, wherein determining whether the bendable segment is in contact with the inner wall of the cavity comprises receiving electrical signals from electrodes, arranged on the bendable segment, contacting the inner wall of the cavity.

5. The apparatus of claim 1, wherein the instructions further cause the computer to determine at least one non-contact curve of the plurality of curves corresponding to at least one respective arrangement of the plurality of different arrangements of the bendable segment determined not to be in contact with the inner wall of the cavity.

6. The apparatus of claim 1, further comprising:
    a plurality of contact electrodes positioned on the bendable segment of the catheter and configured to provide electrical signals when in contact with the inner wall of the cavity, wherein the plurality of contact curves correspond to the bendable segment between contact electrodes of the plurality of contact electrodes determined to be in contact with the inner wall of the cavity.

7. The apparatus of claim 5, wherein the instructions cause the computer to reconstruct the cavity further using a regularization in response to the at least one non-contact curve and a morphological opening or closing of the at least one non-contact curve to estimate which points of the at least one non-contact curve lies necessarily within the cavity.

8. The apparatus of claim 5, wherein the instructions further cause the computer to adapt an adaptable cavity model to the plurality of contact curves and the least one non-contact curve defined by the bendable segment in the different arrangements for reconstructing the cavity.

9. The apparatus of claim 8, wherein the adaptable cavity model is adapted to wrap the at least one non-contact curve.

10. The apparatus of claim 8, wherein the adaptable cavity model is an anatomical model.

11. A method for performing a minimally invasive medical procedure in a cavity of a subject, the method comprising:
    introducing a catheter into the cavity during the minimally invasive medical procedure, wherein the catheter is shape sensing enabled and comprises a bendable segment for being arranged within the cavity in different arrangements during the minimally invasive medical procedure;
    receiving optical shape sensing information from the catheter;
    determining whether the bendable segment of the catheter introduced into the cavity is in contact with an inner wall of the cavity in each arrangement of a plurality of different arrangements of the bendable segment;
    determining a plurality of curves defined by the bendable segment of the catheter introduced into the cavity in different arrangements within the cavity, respectively, using the optical shape sensing information from the catheter
    identifying a plurality of contact curves of the plurality of curves corresponding to respective arrangements of the plurality of different arrangements of the bendable segment of the catheter introduced into the cavity determined to be in contact with the inner wall of the cavity;
    reconstructing the cavity from the plurality of contact curves, such that a reconstructed inner wall of the reconstructed cavity is defined by the plurality of contact curves;
    displaying the reconstructed cavity to provide a map for guiding the catheter in the cavity; and
    performing the minimally invasive medical procedure using the map of the reconstructed cavity.

12. The method of claim 11, further comprising:
    identifying a plurality of non-contact curves corresponding to respective arrangements of the plurality of different arrangements of the bendable segment of the catheter determined to be not in contact with the cavity; and
    adapting a cavity model to the plurality of contact curves and the plurality of non-contact curves defined by the bendable segment in the different arrangements for reconstructing the cavity.

13. The method of claim 11, wherein determining whether the bendable segment is in contact with the inner wall of the cavity comprises receiving electrical signals from contact electrodes, arranged on the bendable segment, contacting the inner wall of the cavity.

14. A non-transitory computer readable medium that stores program code for performing a minimally invasive medical procedure in a cavity of a subject using an optical shape sensing enabled catheter for being introduced into the cavity, wherein the catheter comprises a bendable segment for being arranged within the cavity in a plurality of different arrangements, wherein, when executed by a computer, the program code causes the computer to carry out steps including:

receiving optical shape sensing information from the catheter;

determining whether the bendable segment of the catheter introduced into the cavity is in contact with an inner wall of the cavity in each arrangement of the plurality of different arrangements of the bendable segment;

determining a plurality of curves, defined by the bendable segment of the catheter introduced into the cavity in arrangements of the plurality of different arrangements, respectively, using the optical shape sensing information;

identifying a plurality of contact curves of the plurality of curves corresponding to respective arrangements of the plurality of different arrangements of the bendable segment of the catheter determined to be in contact with the inner wall of the cavity;

reconstructing the cavity from the plurality of contact curves, such that a reconstructed inner wall of the reconstructed cavity is defined by the plurality of contact curves; and displaying, on a display device operatively coupled to the computer, the reconstructed cavity to provide a map for guiding the catheter in the cavity to perform the minimally invasive medical procedure.

15. The non-transitory computer readable medium of claim 14, wherein the program code causes the computer to identify carry out further steps including identifying non-contact curves of the plurality of curves corresponding to respective arrangements of the plurality of different arrangements of the bendable segment determined not to be in contact with the inner wall of the cavity.

16. The non-transitory computer readable medium of claim 15, wherein the program code causes the computer to carry out further steps including adapting an adaptable cavity model to the contact and non contact curves defined by the bendable segment in the different arrangements for reconstructing the cavity.

17. The non-transitory computer readable medium of claim 16, wherein the adaptable cavity model is adapted to wrap the non-contact curves.

18. The non-transitory computer readable medium of claim 16, wherein the adaptable cavity model is an anatomical model.

19. The non-transitory computer readable medium of claim 14, wherein determining whether the bendable segment is in contact with the inner wall of the cavity comprises receiving electrical signals from contact electrodes, arranged on the bendable segment, contacting the inner wall of the cavity.

20. The non-transitory computer readable medium of claim 15, wherein the program code causes the computer to reconstruct the cavity further using a regularization in response to the non-contact curves and a morphological opening or closing of the non-contact curves to estimate which points of the non-contact curves lie necessarily within the cavity.

* * * * *